(12) United States Patent
Tang et al.

(10) Patent No.: US 8,895,590 B2
(45) Date of Patent: Nov. 25, 2014

(54) EPOTHILONE COMPOUNDS, PREPARATION METHOD AND USE THEREOF

(75) Inventors: Li Tang, Beijing (CN); Rongguo Qiu, Beijing (CN)

(73) Assignee: Li Tang, Beijing (CN)

( * ) Notice: Subject to any disclaimer, the term of this patent is extended or adjusted under 35 U.S.C. 154(b) by 0 days.

(21) Appl. No.: 13/526,097

(22) Filed: Jun. 18, 2012

(65) Prior Publication Data
US 2012/0322838 A1 Dec. 20, 2012

Related U.S. Application Data

(63) Continuation-in-part of application No. PCT/CN2010/002078, filed on Dec. 17, 2010.

(51) Int. Cl.
C07D 417/06 (2006.01)
C07D 493/04 (2006.01)
A61K 31/427 (2006.01)

(52) U.S. Cl.
CPC .......... *C07D 417/06* (2013.01); *C07D 493/04* (2013.01)
USPC ......................................... 514/365; 548/204

(58) Field of Classification Search
None
See application file for complete search history.

(56) References Cited

U.S. PATENT DOCUMENTS

2011/0112149 A1  5/2011  Tang et al.

FOREIGN PATENT DOCUMENTS

| CN | 1521258 | 8/2004 |
|---|---|---|
| CN | 1629283 | 6/2005 |
| WO | WO 99/27890 | 6/1999 |

OTHER PUBLICATIONS

Frein et al. New sources of chemical diversity inspired by biosynthesis: rational design of a potent epothilone analogue. Organic Letters, vol. 11, No. 15, 2009, 3186-3189.*
Bollag et al., "Epothilones, a New Class of Microtubule-Stabilizing Agents with a Taxol-like Mechanism of Action", Cancer Research 55, pp. 2325-2333, Jun. 1, 1995.
Gerth et al., "Epothilons A and B: Antifungal and Cytotoxic Compounds from Sorangium Cellulosum (Myxobacteria) Production, Physco-chemical and Biological Properties", The Journal of Antibiotics, pp. 560-563, Jun. 1996.
Frein et al., "New Sources of Chemical Diversity Inspired by Biosynthesis: Rational Design of a Potential Epothilone Analogue", Org. Letter. 11(15), pp. 3186-3189, Aug. 6, 2009.
Altmann et al., "Epothilones and related Structures—a New Class of Microtubule Inhibitors with Potent in Vivo Antitumor Activity", Minireview, Biochima et Biophysics Acta 1470, M79-M91, 2000.
Hofle et al., "Epothilone A and B—Novel 16-Membered Macrolides with Cytotoxic Activity: Isolation, Crystal Structure, and Conformation in Solution", Agnew. Chem. Int. Edition in English, vol. 35, Issue 13-14, pp. 1567-1569, Jul. 1996.
Skehan et al., "New Colormetric Cytotoxicty Assay for Anticancer-Drug Screening", J. Natl. Cancer Inst. 82: pp. 1107-1112, Jul. 1990.
Giannakakou et al., "Combinations of Paclitaxel and Vinblastine and their Effects on Tubulin Polymerization and Cellular Cytotoxity: Characterization of a Synergistic Schedule", Int J. Cancer, 75:, pp. 57-63, Jan. 1998.
Tang et al., "Generation of Novel Epothilone Analogs with Cytotoxic Activity by Biotransformation", The Journal of Antibiotics, vol. 56, No. 1, Jan. 2003, pp. 16-23.

* cited by examiner

*Primary Examiner* — Alicia L Otton
(74) *Attorney, Agent, or Firm* — McDonnell Boehnen Hulbert & Berghoff LLP

(57) ABSTRACT

Epothilone compounds represented by formula (I), their preparation methods and their use for preparing medicines are disclosed. The epothilone compounds are prepared by bioconversion and chemosynthesis or chemical modifications using epothilones or their derivatives as starting materials. Said epothilone compounds can be used to treat proliferative diseases.

14 Claims, 4 Drawing Sheets

EPOTHILONE COMPOUNDS, PREPARATION METHOD AND USE THEREOF

TECHNICAL FIELD

The present invention relates to a series of epothilone compounds and preparation methods thereof, and specifically relates to novel 16-membered cyclic epothilone compounds, preparation method and use thereof, and belongs to the field of medical compounds.

BACKGROUND ART

Epothilone A (EpoA) and epothilone B (EpoB) are among 16-membered cyclic epothilone compounds derived from macrocyclic lactone-based polyketone compounds. They are initially isolated from soil bacteria, *Sorangium cellulosum* strain So ce90, and have the structure below. [Hofle et al., 1996, Angew. Chem. Int. Ed. Engl. 35(13/14): 1567-1569; Gerth et al., 1996. J. Antibiotics 49(6): 560-563]

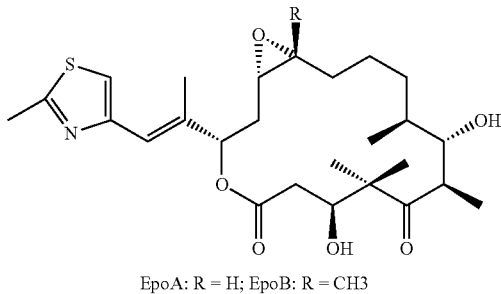

EpoA: R = H; EpoB: R = CH3

Epothilones show great potential in treating cancers. Although being structurally different, epothilones show very similar action mechanisms to those of well-known anti-cancer drug, paclitaxel (Taxol), including inducement of tubulin polymerization and stabilization of the formation of microtubes. These compounds exhibit powerful killing capability on different tumor cell lines. Specifically, they exhibit remarkable effects on multidrug-resistant (MDR) tumor cell lines, especially paclitaxel-resistant tumor cell lines or tumor cell lines having resistance to other anti-tumor drugs [Altmann et al., 2000. Biochem. Biophys. Acta. 1470(3): M79-91; Bollag et al., Cancer Res. 55(11): 2325-2333].

The deoxygenized counterparts of Epothilones A and B, namely Epothilones C and D, have been successfully synthesized via chemical total synthesis. However, they can also be obtained from the ferment extracts of natural epothilone-producing strain, *S. cellulosum*. They can be detected along with many other compounds with epothilone-like structures as trace components.

At present, attentions have been drawn to the development of epothilones and relevant analogues as more effective chemotherapeutants. For example, the naturally-occurring epothilone compounds may be modified by chemical semi-synthesis, such as the reaction converting Epothilone B into the corresponding lactam analogue BMS247550, as described in WO99/27890.

The new epothilone compounds of the present invention having the general formula (I) have beneficial pharmacologic properties, can inhibit the growth of tumor cells, and can be used in the treatment of proliferative disorders. They are prospective to become pioneer compounds for new anti-cancer drugs. Therefore, there is a good prospect for research and development of novel epothilone derivatives.

SUMMARY OF THE INVENTION

According to one aspect of the present invention, there is provided a series of new epothilone compounds or pharmaceutically acceptable salts, hydrates, polymorphs, optical isomers, racemates, diastereoisomers or enantiomers thereof.

According to another aspect of the present invention, there is provided methods for preparing the epothilone compounds of the present invention, including bioconversion and chemical synthesis or chemical modification using Epothilone D or a derivative thereof as a raw material.

According to another aspect of the present invention, there is provided a pharmaceutical composition comprising the compound of the present invention or a pharmaceutically acceptable salt, hydrate, polymorph, optical isomer, racemate, diastereoisomer or enantiomer thereof. In some embodiments, the pharmaceutical composition further comprises one or more pharmaceutical carriers and/or diluents; the pharmaceutical carrier and/or diluent may include at least one inert component such as auxiliary, excipient, preservative, absorption retardant, filler, binding agent, adsorbent, buffer, disintegrant, solubilizer, and the like. Formulating of the composition is well-known in the art.

According to another aspect of the present invention, there is provided a use of the epothilone compound of the present invention or a pharmaceutically acceptable salt, hydrate, polymorph, optical isomer, racemate, diastereoisomer or enantiomer thereof in the preparation of a medicament for treating proliferative disorders.

According to another aspect of the present invention, there is provided a use of an epothilone compound of the present invention or a pharmaceutically acceptable salt, hydrate, polymorph, optical isomer, racemate, diastereoisomer or enantiomer thereof in the preparation of a medicament for inhibiting excessive proliferation of cells and terminating cell growth.

According to another aspect of the present invention, there is provided a method for treating proliferative disorders, comprising administering a therapeutically effective amount of an epothilone compound of the present invention or a pharmaceutically acceptable salt, hydrate, polymorph, optical isomer, racemate, diastereoisomer or enantiomer thereof to a subject in need thereof. The subject is preferably a mammal, especially human.

According to another aspect of the present invention, there is provided a method for inhibiting excessive proliferation of cells and terminating cell growth, comprising contacting the cell with an epothilone compound of the present invention or a pharmaceutically acceptable salt, hydrate, polymorph, optical isomer, racemate, diastereoisomer or enantiomer thereof.

According to another aspect of the present invention, there is provided a method for treating diseases or disorders relevant to excessive proliferation of cells, comprising administering a therapeutically effective amount of an epothilone compound of the present invention or a pharmaceutically acceptable salt, hydrate, polymorph, optical isomer, racemate, diastereoisomer or enantiomer thereof to a subject in need thereof. The subject is preferably a mammal, especially human.

The new epothilone compounds of the present invention are represented by the following general formula (I):

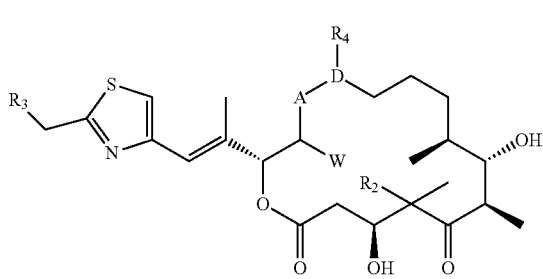

(I)

wherein A-D is carbon-carbon double bond of the following formula (a) or epoxy group of the following formula (b)

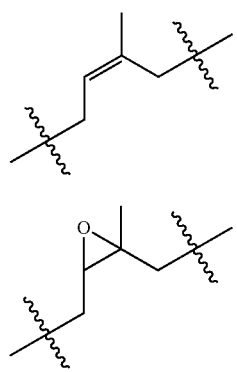

a b

X is O or N—R;

W is $NR_1R$ or O—R, wherein

R is selected from H, hydroxyl or amino protective group, substituted or unsubstituted lower alkyl or unsaturated hydrocarbonyl; preferably H, amino protective group, substituted or unsubstituted $C_{1-6}$ alkyl or $C_{2-6}$ alkenyl, more preferably $CH_3$ or $CF_3$;

$R_1$ is selected from H, OH, substituted or unsubstituted lower alkyl or unsaturated hydrocarbonyl, or forms cycloalkyl together with R (preferably substituted or unsubstituted $C_{1-6}$ alkyl or $C_{2-6}$ alkenyl, or forms $C_{3-6}$ cycloalkyl together with R);

wherein W is more preferably $NH_2$, O—$CH_3$, $NHCH_3$, $N(CH_3)_2$ or

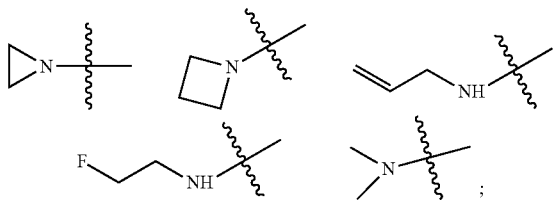

;

$R_2$ is selected from H, substituted or unsubstituted lower alkyl or unsaturated hydrocarbonyl, or forms lower cycloalkyl with the methyl on C-4 position; wherein $R_2$ is preferably H or methyl;

$R_3$ is selected from H, OH or $NH_2$;

$R_4$ is selected from H, substituted or unsubstituted lower alkyl, and $R_4$ is preferably $CH_3$ or $CF_3$;

wherein the general formula (I) does not include 14-OH Epothilone D or 4-demethyl 14-OH Epothilone D.

The present invention also provides pharmaceutically acceptable salts, hydrates, polymorphs, optical isomers, racemates, diastereoisomers or enantiomers of the compounds of the present invention.

The term "lower" as used herein refers to a saturated or unsaturated group having 1-6 carbon atoms, preferably having 1-4 carbon atoms.

Unless otherwise indicated, the term "alkyl" as used herein alone or in combination refers to optionally substituted linear or optionally substituted branched saturated hydrocarbon having from 1 to about 10 carbon atoms, preferably from 1 to about 6 carbon atoms. Examples thereof include but are not limited to methyl, ethyl, n-propyl, iso-propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, iso-butyl, sec-butyl, tert-butyl, n-pentyl, iso-pentyl, neo-pentyl, tert-pentyl and hexyl, as well as longer alkyl such as heptyl and octyl, etc.

Unless otherwise indicated, the term "cycloalkyl" as used herein alone or in combination refers to optionally substituted saturated hydrocarbon ring which comprises from 3 to about 15 ring-forming carbon atoms, from 3 to about 10 ring-forming carbon atoms, or from 3 to about 6 ring-forming carbon atoms, and may further comprise other non-ring-forming carbon atoms as a substituent (e.g., methylcyclopropyl).

Unless otherwise indicated, the term "unsaturated hydrocarbonyl" as used herein alone or in combination includes alkenyl having one or more C=C double bonds and alkynyl having one or more C≡C triple bonds, wherein alkenyl refers to optionally substituted linear or optionally substituted branched hydrocarbonyl having from 2 to about 10 carbon atoms, preferably from 2 to about 6 carbon atoms. The double bond in these groups may be cis- or trans-configuration, and should be construed as encompassing these two kinds of isomers. Examples thereof include but are not limited to vinyl ($CH=CH_2$), 1-propenyl ($CH_2CH=CH_2$), isopropenyl ($C(CH_3)=CH_2$), butenyl, 1,3-butdienyl, and the like. Alkynyl refers to optionally substituted linear or optionally substituted branched hydrocarbonyl having one or more C≡C triple bonds and from 2 to about 10 carbon atoms, preferably from 2 to about 6 carbon atoms. Examples thereof include but are not limited to acetylenyl, 2-propynyl, 2-butynyl, 1,3-butdiynyl, and the like.

Unless otherwise indicated, "amino protective group" as used herein alone or in combination may be any appropriate amino protective group well-known in the art, including alkoxycarbonyl, acyl and alkyl. Examples thereof include but are not limited to tert-butoxycarbonyl, benzoxycarbonyl, allyloxycarbonyl, trimethylsilylethoxycarbonyl, methoxycarbonyl, ethoxycarbonyl, 2-biphenyl-2-propoxycarbonyl, phthalyl, p-toluene sulfonyl, benzoyl, p-nitrophenyl sulfonyl, triphenylmethyl, formyl, trifluoroacetyl, benzyl, p-methoxybenzyl, 2,4-dimethoxybenzyl, and the like.

In the above definitions, as in the definitions of R, $R_1$, $R_2$ and $R_4$, the substituent for substituted alkyl or substituted unsaturated hydrocarbonyl may be halogen, trifluoromethyl, trifluoromethoxy, alkanoyl, aryloxy, amino, alkylamino, heterocyclylamino, arylamino, aralkylamino, alkanoylamino, alkylsulfonyl, thioalkyl, alkoxycarboxyl, etc.

Epothilone A and Epothilone B are initially isolated from soil bacteria *Sorangium cellulosum* strain So ce90. Therefore, Epothilones A and B may be readily obtained by isolating the fermentation. As disclosed in CN1629283A which was published on Jun. 22, 2005, Epothilones C or D (wherein $R_4$ is H or $CH_3$) may be readily obtained for example by inactivating gene P450 of epothilone biosynthesis genes, which causes natural Epothilones A and B-producing bacteria to produce Epothilone C or D as main metabolite. As disclosed in CN1521258A published on Aug. 18, 2004, 4-demethyl Epothilones A and B or C and D may be readily obtained generally by inactivating the MT trans-methyl domain in extender module 8 of the epothilone biosynthesis genes, which causes natural epothilone-producing bacteria to produce 4-demethyl epothilones as main metabolites. WO99/27890 discloses a transformation reaction wherein Epothilone B is transformed to corresponding lactam analogue BMS247550. These three patent documents are incorporated herein by reference.

In another aspect, the present invention relates to the synthesis of a compound wherein S may be replaced by O, from an oxazole counterpart of an epothilone derivative. As disclosed in CN1521258A, bacteria normally producing thiazole epothilone compound are modulated in a way facilitating the production of oxazole counterpart by supplementing an excess amount of serine to the bacteria.

Among the compound of general formula (I), 14-amino epothilone derivative thereof may be prepared by bio-transformation of Epothilone D or 4-demethyl Epothilone D derivative to obtain 14-OH Epothilone D or 4-demethyl 14-OH EpothiloneD, and chemical modification.

Synthesis Scheme 1:

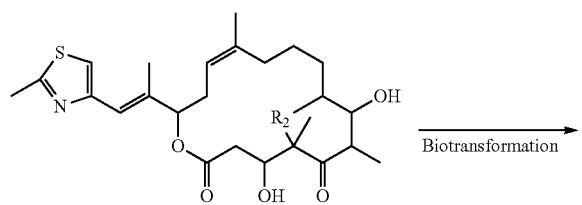

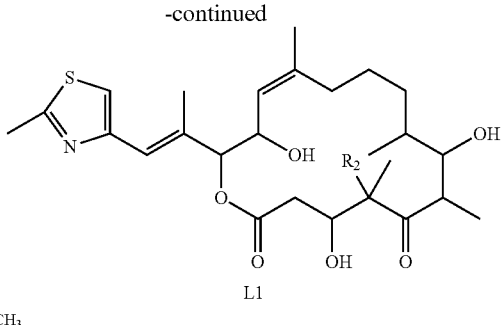

$R_2$ = H or $CH_3$

As described in Synthesis Scheme 1, Epothilone D or a derivative thereof may be firstly hydroxylated at C-14 position using a microbe or a hydroxylase derived therefrom. This kind of C-14 hydroxylated epothilone derivatives LI may also be obtained with the microbic transformation described in Example 1. As disclosed in CN1629283A published on Jun. 22, 2005, Epothilone C or D may be readily obtained for example by inactivating gene P450 of epothilone biosynthesis genes, which causes natural Epothilones A and B-producing bacteria to produce Epothilone C or D as main metabolite. As disclosed in CN1521258A published on Aug. 18, 2004, 4-demethyl Epothilones A and B or C and D may be readily obtained generally by inactivating the MT trans-methyl domain in extender module 8 of the epothilone biosynthesis gene, which causes natural epothilone-producing to produce 4-demethyl epothilones as main metabolites. These two patent documents are incorporated herein by reference.

Further preferred compounds of general formula (I) wherein W=$NH_2$ may be prepared from C-14 hydroxylated Epothilone D derivatives by the general method described in the chemical Synthesis Scheme 2. This kind of compounds may also be prepared with the method described in Example 2.

Synthesis Scheme 2:

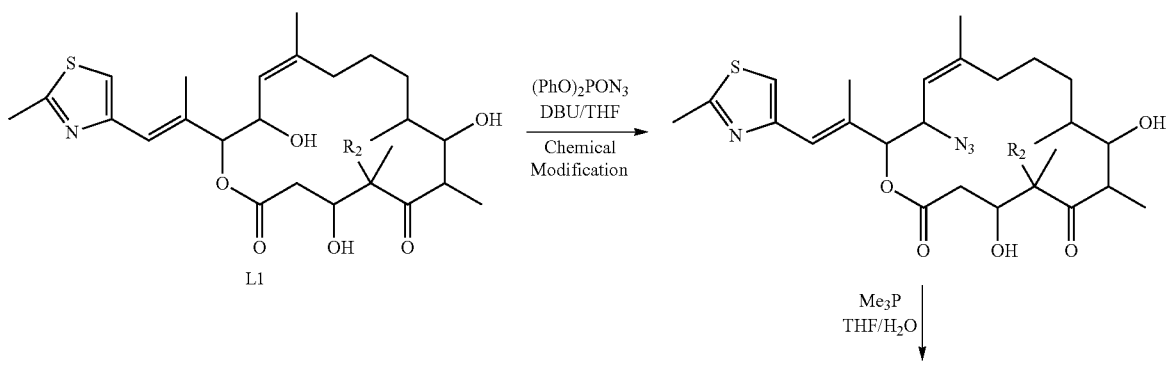

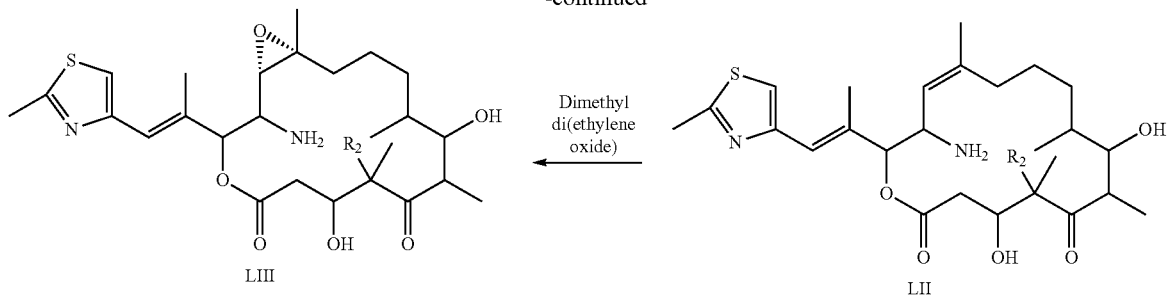

An appropriate group, such as triethylsilyl, butyldimethylsilyl, or the like, may be used to protect free hydroxyls 3- and 7-OH in the compound LI, the protective groups being designated as P1 and P2, respectively. The protective group P3 for 14-OH may be selectively removed by AcOH in THF under conditions which do not lead to removal of protective groups P1 and P2.

Allyl palladium π coordinate is formed from a 3- and 7-protected or unprotected Epothilone D derivative by using tetrakis(triphenylphosphine)palladium, and is then treated with primary amine, or reacted with diphenylphosphorylazide and diazobicycloundec-7-ene (DBU) to obtain 14-azido epothilone, which is then reduced with trimethylphosphine and a $NH_4OH$ aqueous solution to give a 3- and 7-protected 14-amino-epothilone derivative, which is deprotected to give compound LII. This type of compounds may be prepared through a chemical epoxidation as described in Example 2.

The protective groups may be present in precursors of 14-OH epothilone compounds, and should protect the relevant functional groups from undesired side reactions, such as acylation, etherification, oxidation, solvolysis, and the like. The protective groups are characterized in that they themselves are ready to be removed by solvolysis, reduction, photolysis or by the action of enzymes, and do not exist in final products. For examples, protective groups may be present in the 3-, 7- and 14-OH free hydroxyls of the precursor 14-OH epothilone, and are designated as P1, P2 and P3, respectively. Before being chemically modified, the P3 protective group for 14-OH may be selectively removed by AcOH in THF under conditions which do not lead to removal of protective groups P1 and P2. The resulted compound is finally amidated to obtain protected compound LII, which is deprotected with methods known in the art to remove P1 and P2. When P1 and P2 are silylethers, such as TMS, TES or TBS, deprotection may be carried out by treating with an acid, such as HF-pyridine in dichloromethane or trichloroacetic acid to obtain LII.

A preferably further modified compound LII is an epoxide (12,13-epoxy derivative), which may be prepared through a chemical epoxidation as described in Example 3.

The hydroxyl protective groups and N-protective groups involved in the definitions of the compounds of the present invention are commonly used protective groups in the art. For example, hydroxyl protective groups are preferably silylethers, such as TMS, TES or TBS; N-protective groups are preferably tert-butyl carboxylic acids, etc. In the preparation of the compound of the present invention, in process steps which are carried out as needed, the functional groups in the starting compound which should not participate in the reaction may be present in the unprotected form or may be protected by one or more protective groups or entirely or partially removed. The protective groups are characterized in that they themselves are ready to be removed by solvolysis, reduction, photolysis or by the action of enzymes, and do not exist in final products. Hydroxyl protective groups are preferably lower alkyl silyl type hydroxyl protective groups as disclosed herein, which may be introduced as needed with a method similar to that described herein and removed as needed, wherein selective protection or deprotection is also possible. In the present application, some protective groups are not mentioned where may be used appropriately, but a person skilled in the art understands when a protective group should or must be used.

Compound LII may also be prepared with the synthesis scheme 2B shown below:

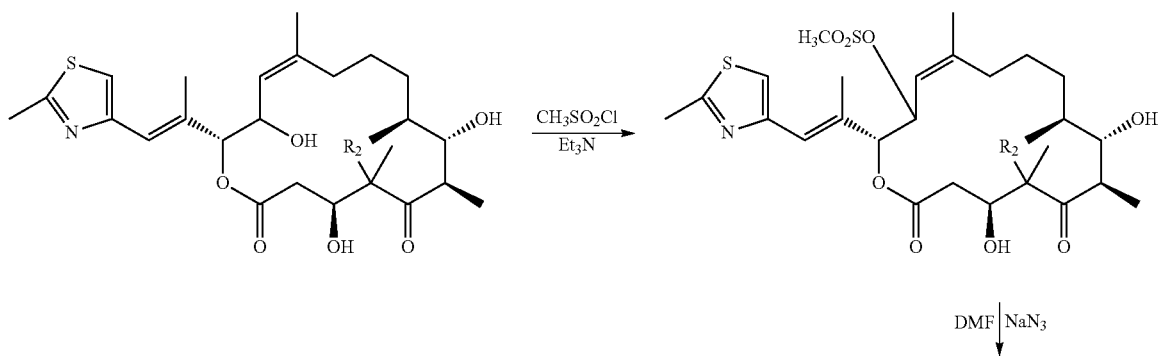

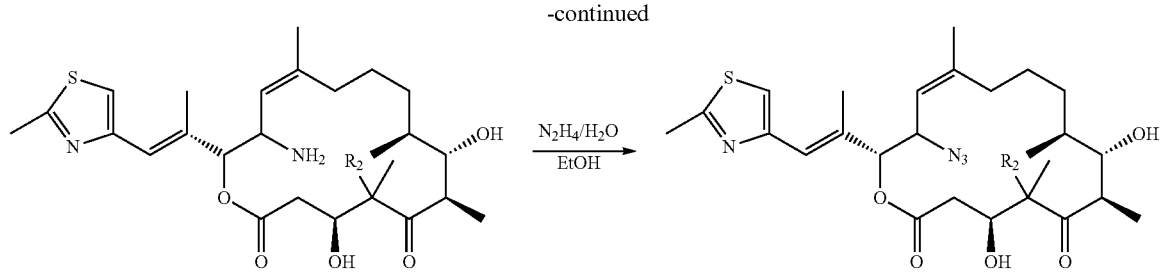

Further preferred compound of general formula (I) wherein W=NRR$_1$ may be prepared by the general method described in Synthesis Scheme 3, wherein NRR$_1$- or NHR$_1$-epothilone compound is prepared from a C-14 hydroxy or methoxy or amino epothilone derivative, and when the compound is a derivative of Epothilone D, a 12-,13-epoxide may be prepared through chemical epoxidation as described in Example 3.

Synthesis Scheme 3:

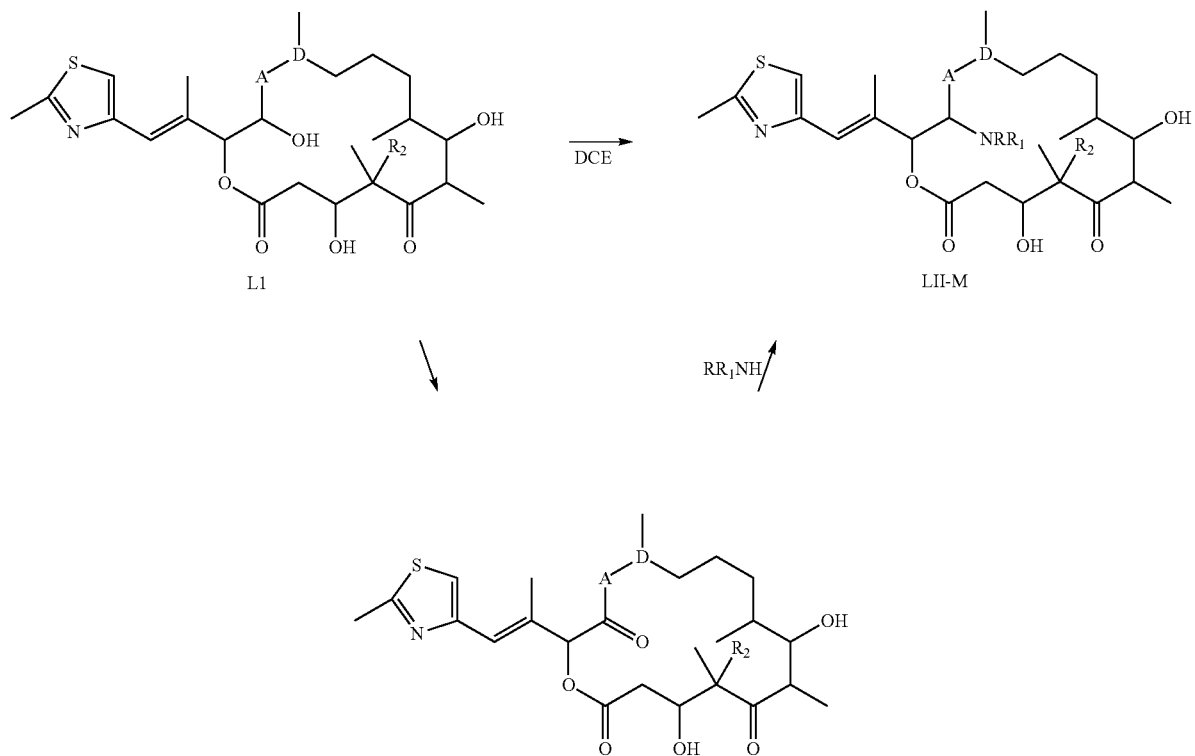

wherein A-D is carbon-carbon double bond of the following formula (a) or epoxy group of the following formula (b):

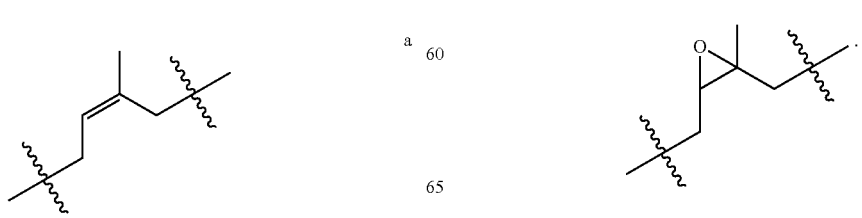

For example:

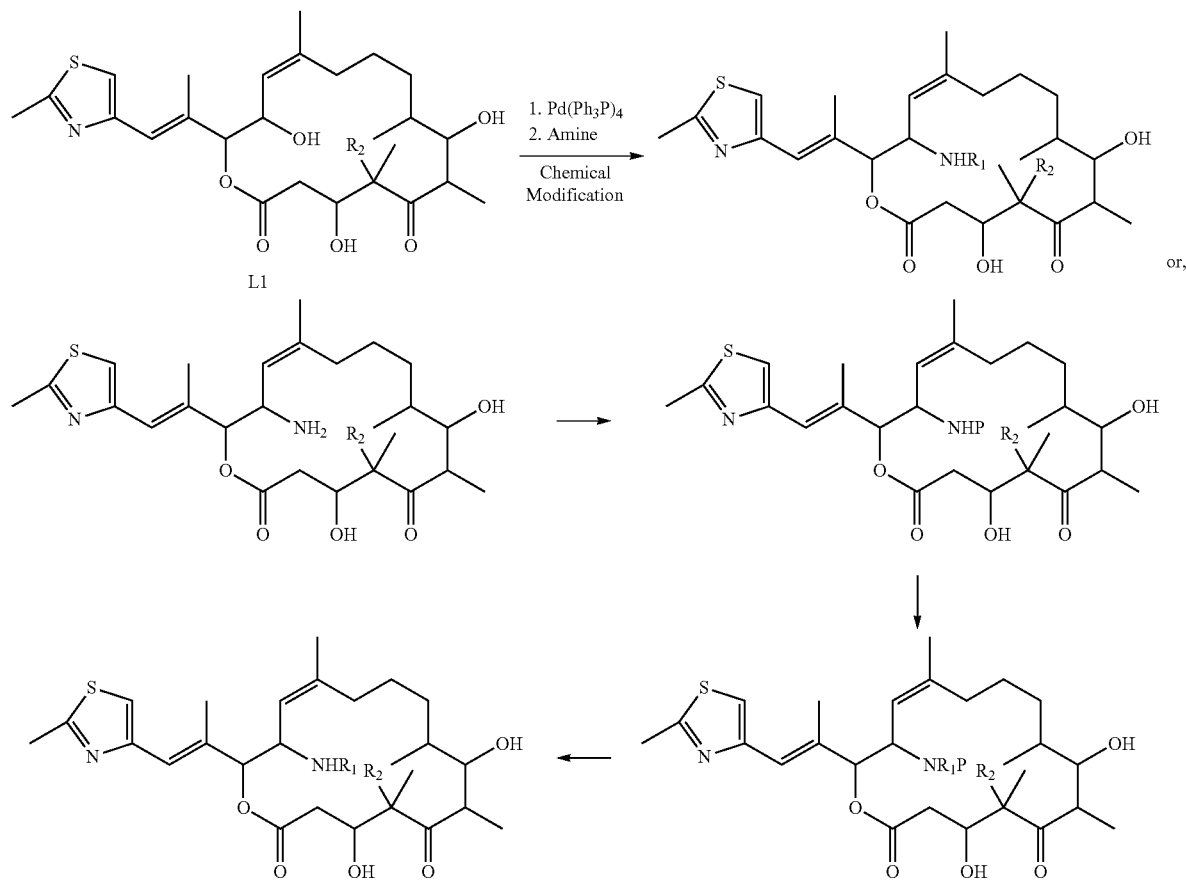

N-protection is carried out with vinyl glycine, where P is t-butyloxycarbonyl suitable for N-protection.

Wherein R1 is not H, the compound is N-alkylated with alkyl halide in the presence of an alkali such as sodium hydroxide.

Deprotection is effected to give a $NHR_1$-compound.

Further preferred compound of general formula (I) wherein W=O—$CH_3$ may be prepared from C-14 hydroxylated Epothilone D derivatives by the general method described in Synthesis Scheme 4. 14-methoxy Epothilone D compound may be prepared by the synthesis method described in Example 4.

-continued

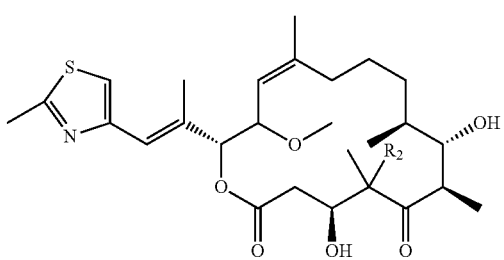

Further preferred compound of general formula (I) is lactam derivative wherein X=NH. This type of compounds may be prepared by the method described in Synthesis Scheme 5.

Synthesis Scheme 4:

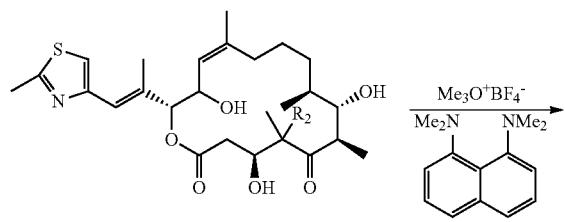

Synthesis Scheme 5:

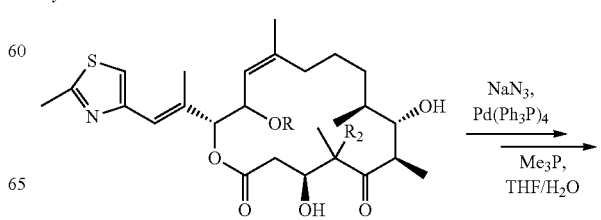

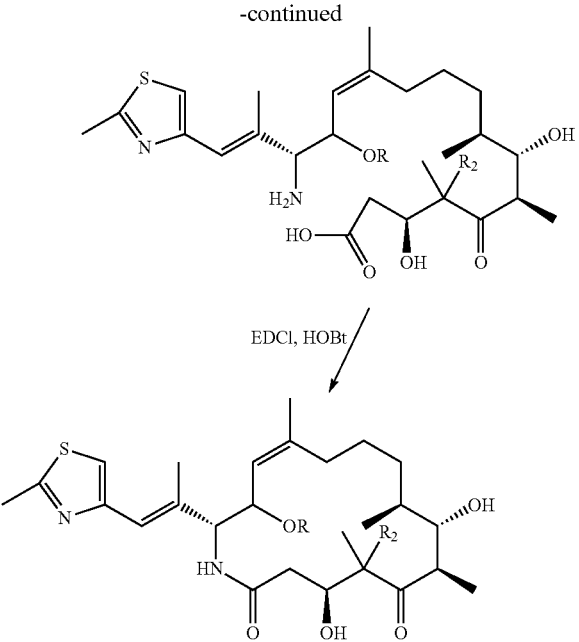

EDCl, HOBt

Further preferred compound of general formula (I) is 21-R derivative wherein $R_3$=OH, $NH_2$. This type of compounds may be prepared by the method described in Synthesis Scheme 6.

Synthesis Scheme 6:

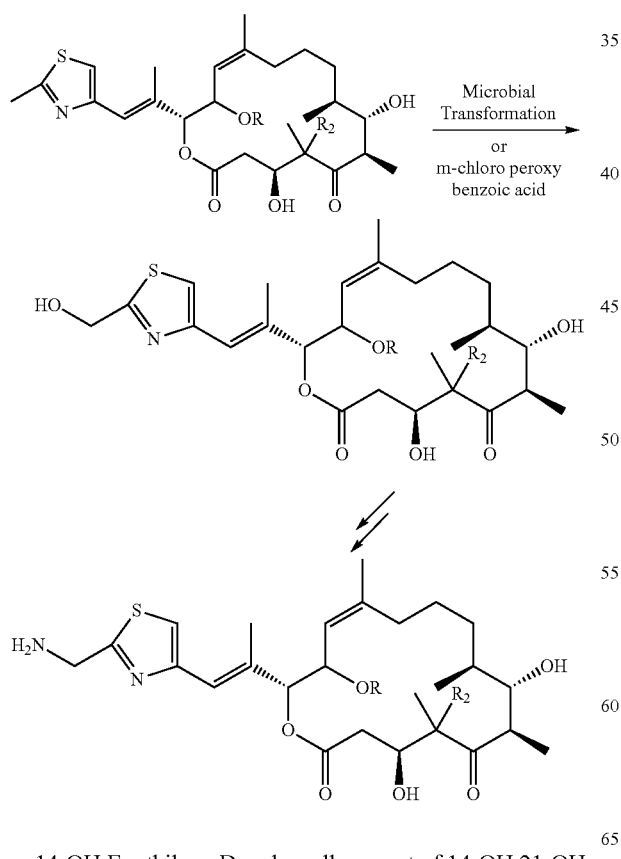

14-OH Epothilone D and small amount of 14-OH,21-OH Epothilone D may be obtained from Epothilone D by the microbial transformation described in Example 1. 14-OH,21-OH Epothilone D may also be obtained from 14-OH Epothilone D following the microbial transformation disclosed in CN1521258A, which was published on Aug. 18, 2004.

Further preferred compound of general formula (I) is epoxide (12,13-epoxy derivative). This type of compounds may be prepared by the general method described in Synthesis Scheme 7.

Synthesis Scheme 7:

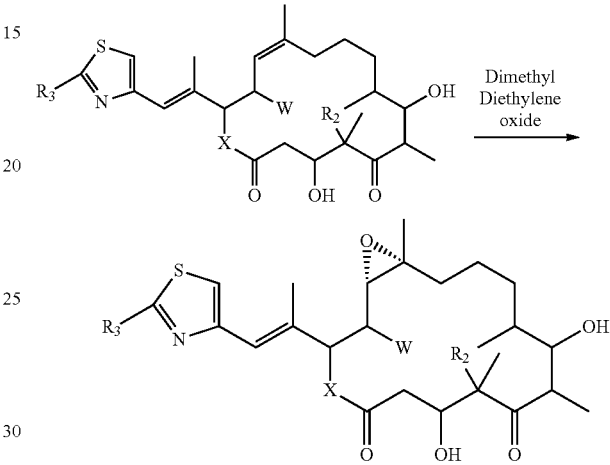

In other embodiments, the present invention provides a compound of general formula (I) which is selected from the compounds with the following structures:

II-A

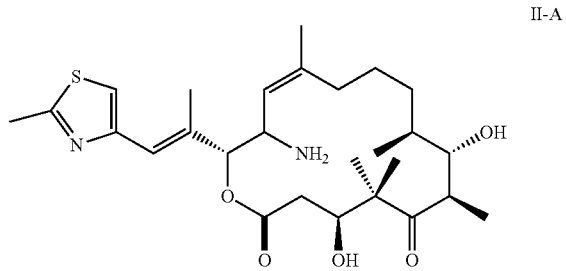

II-B

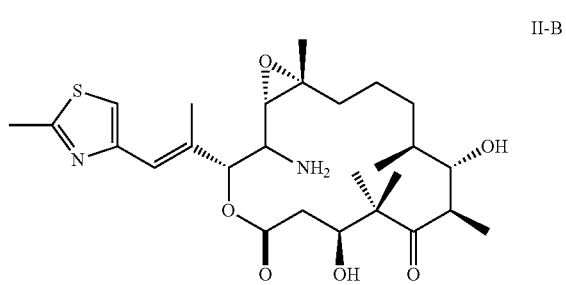

II-C
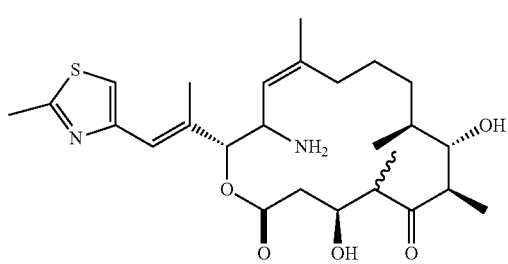
II-D
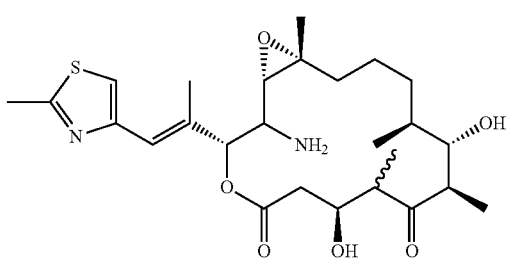
II-E
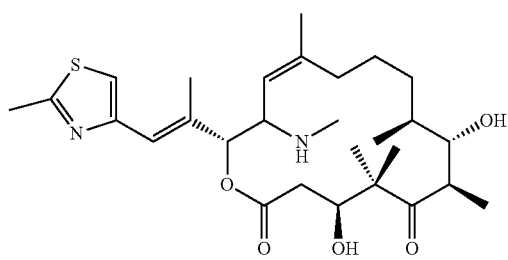
II-F
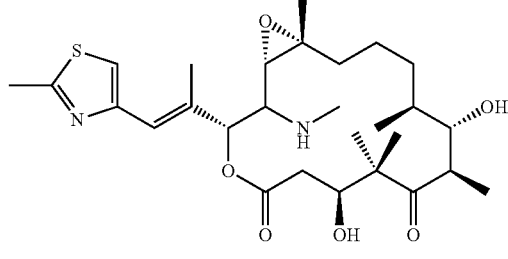
II-H
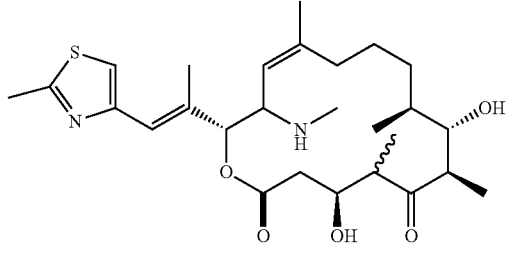
II-J
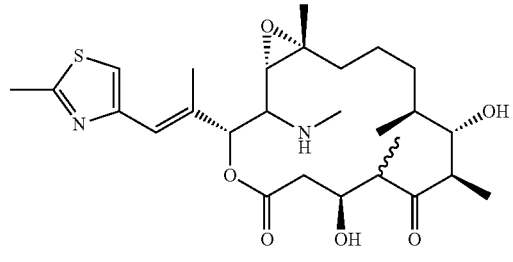
II-K
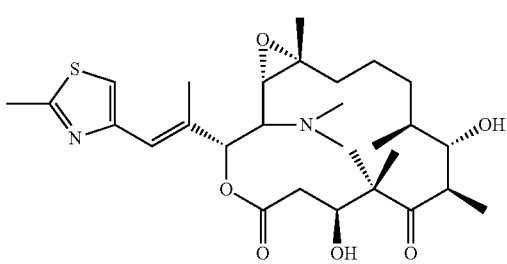
II-L
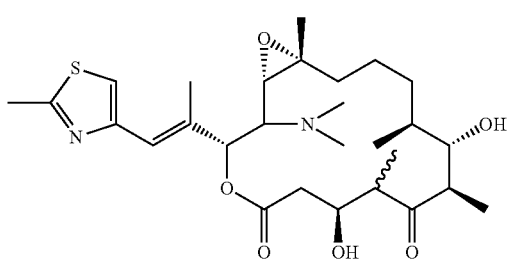
II-M
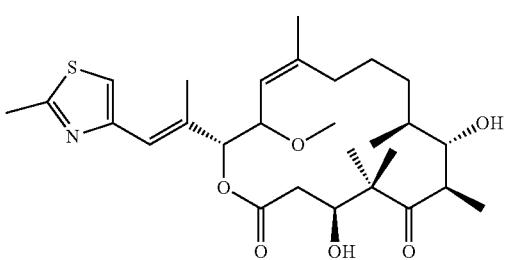
II-N
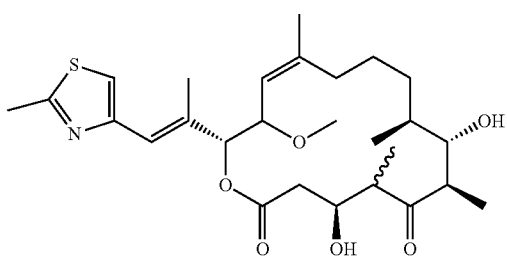
II-O
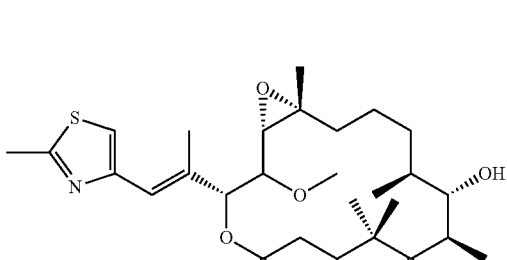
II-P
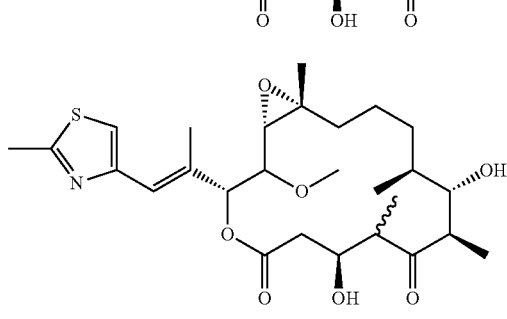

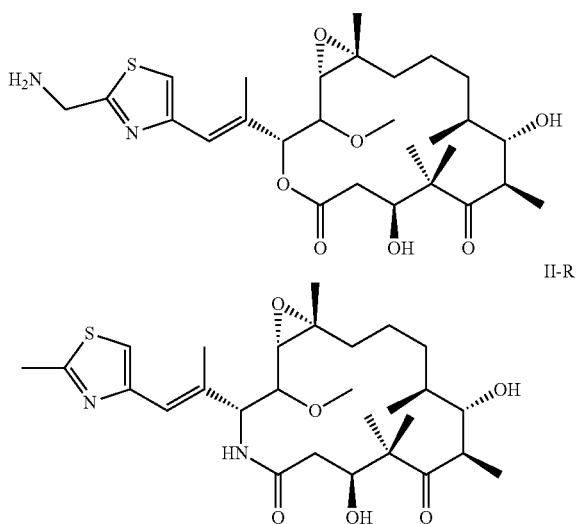

The compounds of the present invention may be screened by conventional analytical methods known in the art. For example, cytotoxicity of a compound may be determined according to SRB analysis described in Skehan et. al., J. Natl. Cancer Inst. 1990, 82: 1107, which is incorporated herein by reference.

The compound of the present invention may be screened for their tubulin polymerization using the conventional analytical method known in the art. For example, the compounds may be screened for their tubulin polymerization according to the method described in Gianakakou et. al., Intl. J. Cancer, 1998, 75: 63, which is incorporated herein by reference.

The present invention further provides a pharmaceutical composition, which comprises a compound of the present invention or a pharmaceutical acceptable salt, hydrate, polymorph, optical isomer, racemate, diastereomer or enantiomer thereof, and one or more conventional pharmaceutical carriers and/or diluents. This type of composition may comprise at least one of auxiliary, excipient, preservative, absorption retardant, filler, binding agent, adsorbent, buffer, disintegrant, solubilizer, and other carrier or inert components. The formulation process of the composition is well known in the art.

In addition to the compound of the present invention or a pharmaceutical acceptable salt, hydrate, polymorph, optical isomer, racemate, diastereomer or enantiomer thereof, the pharmaceutical composition of the present invention may further comprise one or more active drugs, such as other anti-proliferative drugs.

The compound of the present invention may be used in the preparation of a medicament for treating proliferative disorders. The compound of the present invention may also be used in the preparation of a medicament inhibiting excessive proliferation of cells and terminating cell growth. Said proliferative disorders are preferably selected from the group consisting of tumors, multiple sclerosis, rheumatoid arthritis, atherosclerosis and restenosis.

The present invention provides a method for treating proliferative disorders using a compound of the present invention, comprising administrating a therapeutically effective amount of an epothilone compound of the present invention or a pharmaceutically acceptable salt, hydrate, polymorph, optical isomer, racemate, diastereoisomer or enantiomers thereof to a patient in need thereof. The patient is preferably a mammal, more preferably human. The proliferative disorders are preferably selected from the group consisting of tumors, multiple sclerosis, rheumatoid arthritis, atherosclerosis and restenosis.

The present invention further provides a pharmaceutical composition for treating proliferative disorders, wherein said proliferative disorders are preferably selected from group consisting of tumors, multiple sclerosis, rheumatoid arthritis, atherosclerosis and restenosis.

The present invention provides a method for inhibiting excessive proliferation of cells and terminating cell growth, comprising contacting the cell with an epothilone compound of the present invention or a pharmaceutically acceptable salt, hydrate, polymorph, optical isomer, racemate, diastereoisomer or enantiomer thereof.

The present invention provides a method for treating diseases or disorders related to excessive proliferation of cells, comprising administrating a therapeutically effective amount of an epothilone compound of the present invention or a pharmaceutically acceptable salt, hydrate, polymorph, optical isomer, racemate, diastereoisomer or enantiomers thereof to a patient in need thereof. The patient is preferably a mammal, more preferably human.

The compound of the present invention can be of a free form or forms such as prodrug or a salt or ester of the compound of the present invention. The compound of the present invention may be of any form, such as solid, semi-solid or liquid. The pharmaceutical composition may comprise at least one cyclodextrin and pharmaceutical acceptable carriers such as alcohols (ethanol, ethylene glycol, propylene glycol), polyoxyethylene glycol (PEG), Tween, Solutol or the like. The compound of the present invention may be formulated with a pharmaceutical acceptable carrier or diluent for oral, intravenous or subcutaneous administration. The pharmaceutical composition may be formulated according to standard methods employing solid or liquid carriers, diluents and additives suitable for the desired routes of administration. For oral administration, the compound of the present invention may be administered in the form of tablet, capsule, granule, powder and the like. The dosage range of the compound of the present invention is from about 0.05 to 200 mg/kg/day, which can be administered in a single dose or in a multiple dose of 2 to 5 portions.

The formulation of the compound of the present invention may be prepared by other known method for preparing formulation containing drug of low water solubility. For example, the compound may be formulated into an emulsion with vitamin E and/or PEG polyacrylate derivatives (see WO00/71163 and U.S. Pat. No. 6,458,373 B1). Generally, the compound of the present invention is firstly dissolved in ethanol, followed by addition of vitamin E and/or PEG polyacrylate derivatives to form a therapeutic solution. Ethanol is removed, and a precursor emulsion is formed; or the precursor emulsion may be prepared by adding an aqueous solution comprising a surfactant (stabilizer). For intravenous injection, the precursor emulsion may be dispersed to form a homogenous emulsion. For oral administration, the precursor emulsion is normally placed in a gel capsule.

Based on the its effect as an inhibitor of tubulin disassembly, the action mechanism of the compound of general formula (I) and that of the anti-tumor agents paclitaxel and Epothilone are very similar, in which the function of cellular microtubule is disturbed mainly due to the induction of tubulin polymerization and stabilization of microtubule assembly, which results in the inhibition of cell division, cell migration and the intracellular signal transmission and protein excretion, because all those events depend on the rapid and effective disassembly of the microtubule. Therefore, the compound of general formula (I) has excellent pharmacological properties and can be used to inhibit the growth of tumor cells, effectively treat many proliferative disorders, such as solid tumors, liquid tumors such as leukemia, etc., and can also be used to inhibit excessive proliferation of cells and terminate cell growth. Therefore, the compound of the present invention has broad application prospect.

SPECIFIC EMBODIMENTS

The present invention will be further illustrated with examples, but it is not limited thereto.

EXAMPLE 1

Biotransformation for the Formation of 14-Hydroxylated Epothilone D Derivatives

A small freezing tube (1 ml) of *Streptomyce* sp. strain ATCC55098 is inoculated in 5 ml of seed medium (20 g/L glucose, 20 g/L peptone, 10 g/L Yeast Extract, pH=7.0 as adjusted with NaOH; used after sterilization), and then is cultured in a shaking incubator at 30° C. for 2 days. Then, 2.5 ml culture is transferred to 50 ml of fermentation medium (30 g/L baker's yeast; 15 g/L corn syrup, 1 g/L CaCO$_3$, 45 g/L cornstarch, 23.8 g/L HEPES, 20 g/L dextrin, pH=7.0 as adjusted with NaOH; used after sterilization) in a flask, and is cultured at 30° C. for 24 hours. 5-10 mg Epothilone D or a derivative thereof such as 4-demethyl Epothilone D is added to the culture medium, and further cultured for 2-3 days. The transformation product is isolated and 14-hydroxylated Epothilone derivative is recovered from the cultures.

Figure 1:
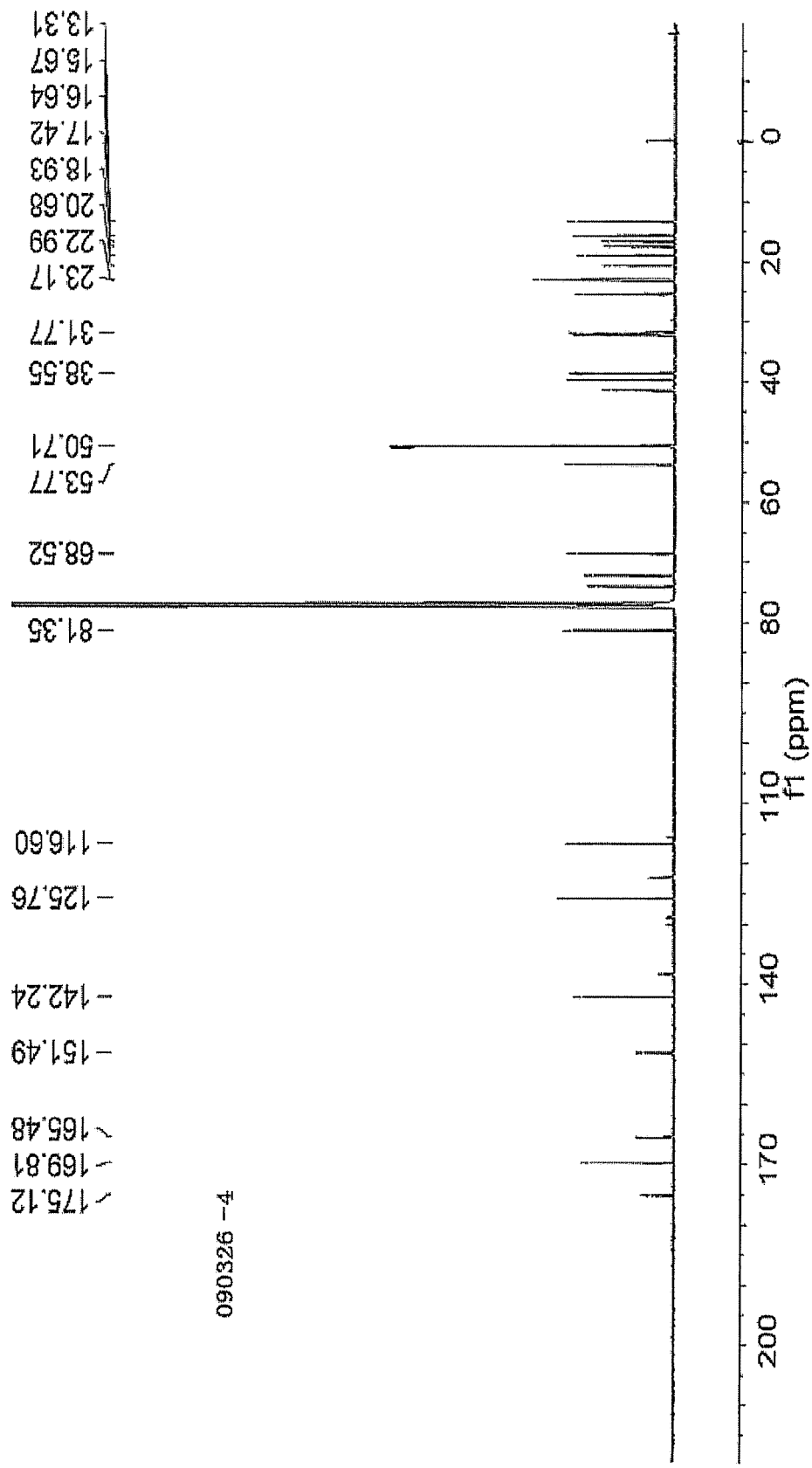
FIG. 1 is the $^1$H-NMR spectrum of 14-OH Epothilone D.
Figure 2:
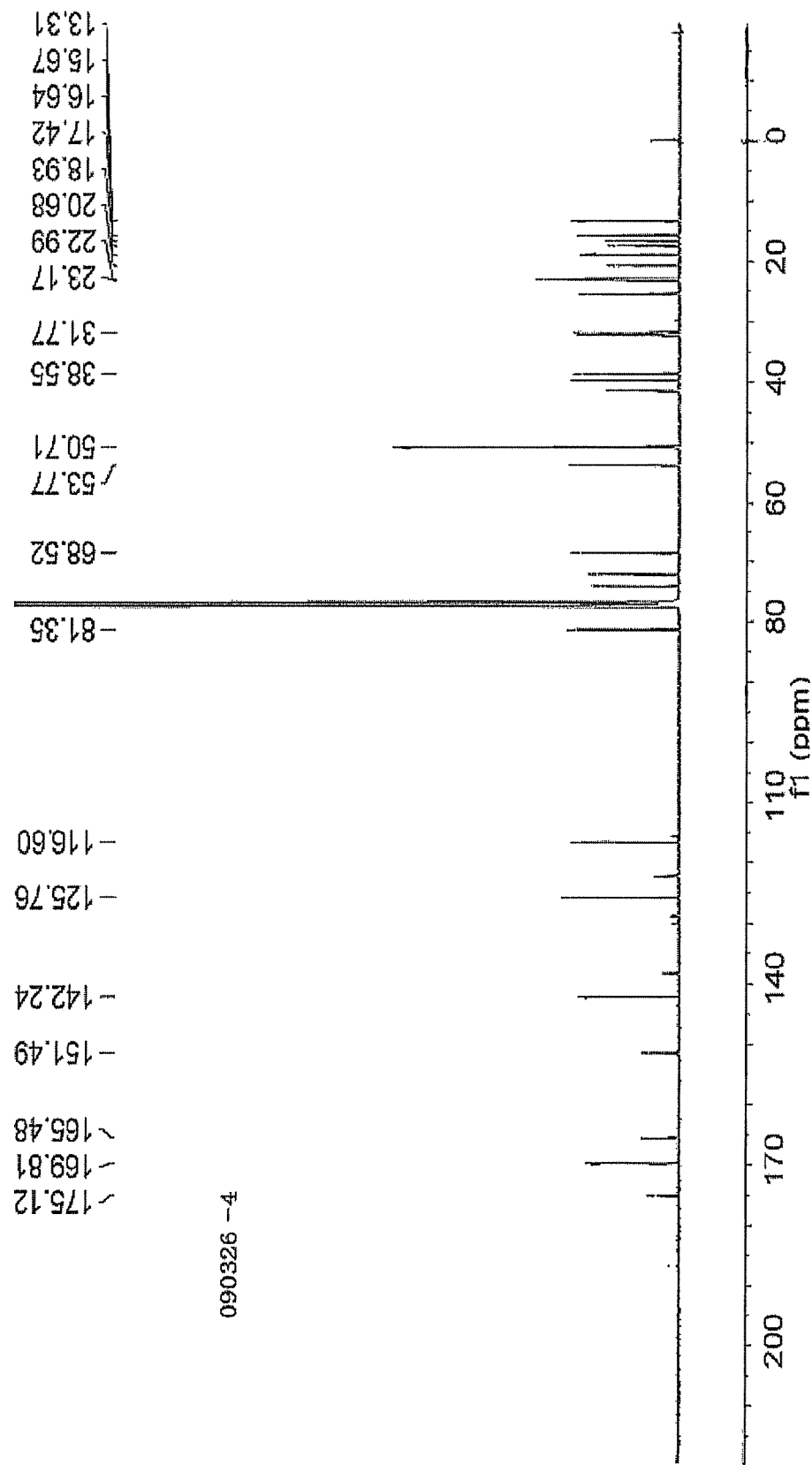
FIG. 2 is the $^{13}$C-NMR spectrum of 14-OH Epothilone D.
Figure 3:
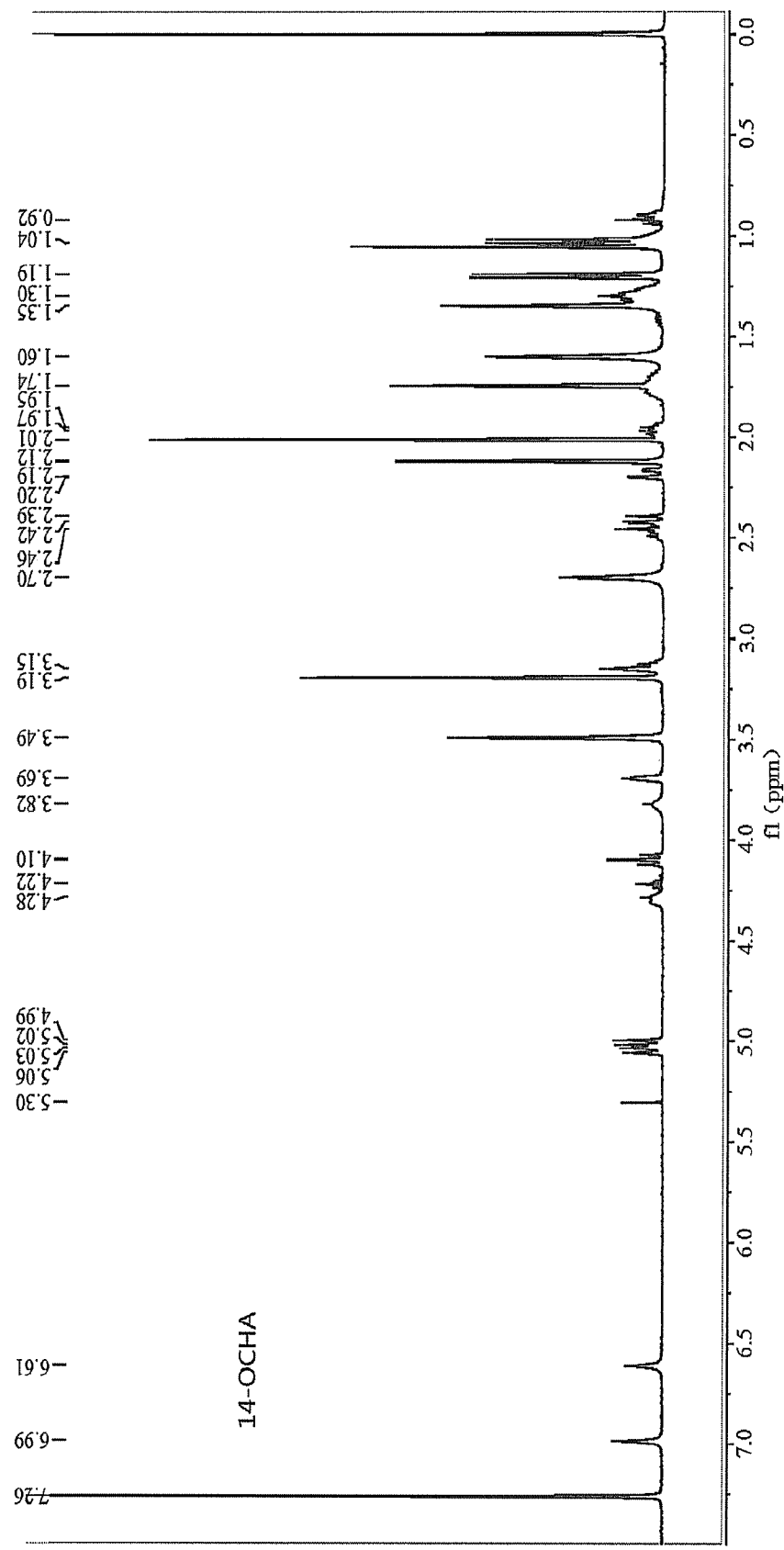
FIG. 3 is the $^1$H-NMR spectrum of 14-O—CH3 Epothilone D.
Figure 4:
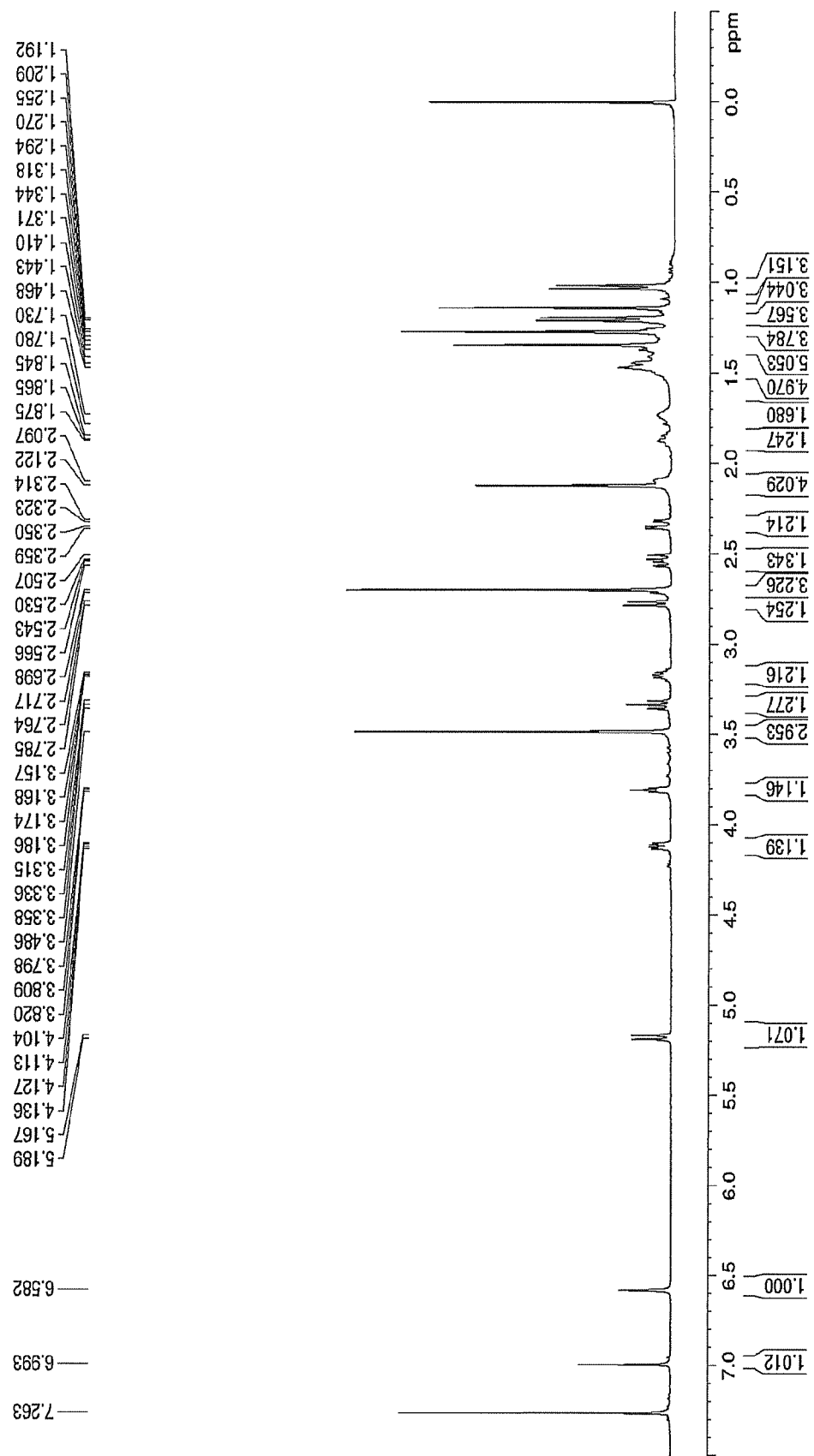
FIG. 4 is the $^1$H-NMR spectrum of 14-O—CH3 Epothilone B.

MS (ESI+) of 14-hydroxy Epothilone D (C$_{27}$H$_{41}$NO$_6$S): 508.26 [M+H]$^+$ $^1$H-NMR and $^{13}$C-NMR spectra of the compound are shown in FIGS. 1 and 2.

MS (ESI+) of 14-hydroxy-21-hydroxy Epothilone D (C$_{27}$H$_{41}$NO$_7$S): 524.26 [M+H]$^+$

EXAMPLE 2

Preparation of 14-NH$_2$ Epothilone D

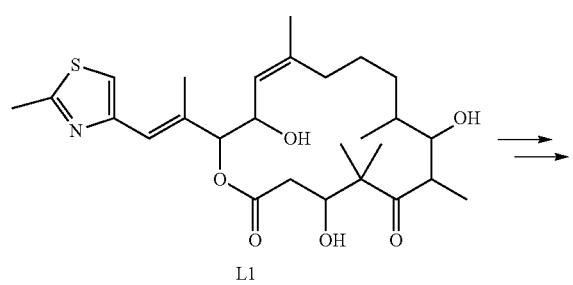

L1

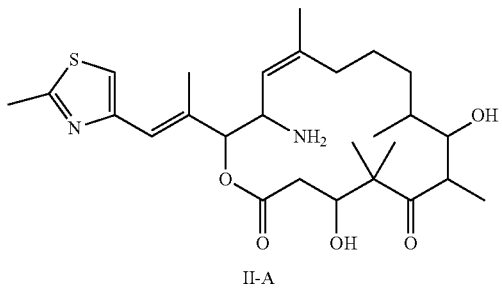

II-A

1. A solution of 7-O-(tert-butyldimethylsilyl)-14-OH Epothilone D (30 mg) in 1.5 ml anhydrous THF is cooled to 0° C. under argon, and treated with diphenylphosphoryl azide (15.5 μl) for 5 minutes, followed by adding 8.8 μl of 1,8-diazabicyclo(5.4.0)undec-7-ene (DBU). The reaction is stirred at 0° C. for 2 hours, and then warmed to room temperature and stirred for further 20 hours. The solution is added with 30 ml ethyl acetate, and washed with water (2×10 ml). The combined aqueous phase is extracted with ethyl acetate (2×15 ml), dried over Na$_2$SO$_4$, filtered and evaporated. 7-O-(tert-butyldimethylsilyl) protected 14-azide Epothilone is purified by SiO$_2$ chromatography.

2a. A solution of the azide (14 mg) obtained from the above step and trimethylphosphine (in 33 μl 1 M THF solution) in 0.3 ml THF is stirred for 5 minutes, and treated with 80 μl of water, and further stirred for 3 hours, until azide is completely consumed. Phosphoryl imine is completely converted to amine upon addition of 50 μl of a 28% NH$_4$OH aqueous solution. After being stirred at 25° C. (room temperature) for 1 hour, the solvents in the mixture are evaporated under vacuum. Chromatographic separation is performed with silica gel (10% methanol in chloroform solution) to afford 3,7-O-(tert-butyldimethylsilyl) protected 14-amino Epothilone.

2b. Another method: 18 mg of Lindlar catalyst is suspended and saturated in 0.5 ml ethanol, followed by adding the azide obtained from the above step and dissolved in ethanol-methanol mixture, and being stirred at room temperature for 30 minutes. The resulting suspension is filtered through diatomite, washed with ethyl acetate, and dried under vacuum.

3. Deprotection: the protected product (67 mg) is dissolved in 1.5 ml THF, and treated with hydrogen fluoride-pyridine (0.6 ml) at 0° C. After 20 minutes, the reaction is warmed to room temperature, and kept at this temperature for 5 hours, and then cooled to 0° C. again. Methoxytrimethylsilane (6 ml) is slowly added, and the mixture is warmed to room temperature, and then subjected to evaporation to afford an oily product, which is then purified by SiO$_2$ chromatography and a pure product is thus obtained.

MS (ESI+) of 14-NH$_2$ Epothilone D compound II-A (C$_{27}$H$_{42}$N$_2$O$_5$S): 507.3 [M+H]$^+$

EXAMPLE 3

Preparation of 14-NH$_2$ Epothilone B

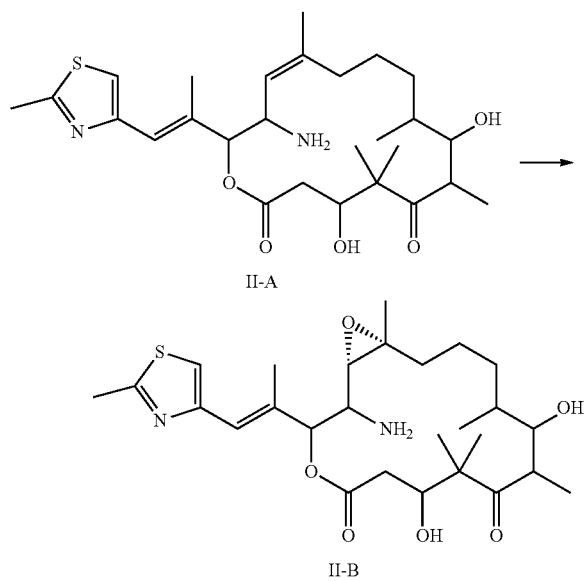

The present example describes the epoxidation of the compound of formula (I) wherein A-Q links together to form a C=C bond.

To a solution of the deoxygenated compound (505 mg) of the present invention in 10 ml CH$_2$Cl$_2$ is added dropwise a solution of dimethyldiethylene oxide (0.1 M in acetone, 17 ml) at −78° C. The mixture is heated to −50° C., and kept at this temperature for 1 hour, followed by adding another portion of the dimethyldiethylene oxide (5 ml). The reaction is proceeded for another 1.5 hours at −50° C. The reactants are dried at −50° C. in nitrogen vapor. The product is purified by SiO$_2$ chromatography.

MS (ESI+) of 14-NH$_2$ Epothilone B compound II-B (C$_{22}$H$_{42}$N$_2$O$_6$S): 523.3 [M+H]$^+$ This general procedure may be suitably applied in preparing corresponding 12,13-epoxy derivatives from other compounds of the present invention, such as 14-N(CH$_3$)$_2$ Epothilone B Compound II-L.

EXAMPLE 4

Preparation of 14-Methoxy Epothilone

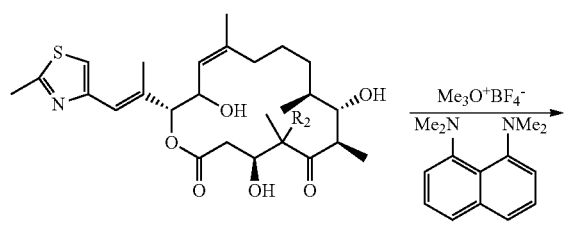
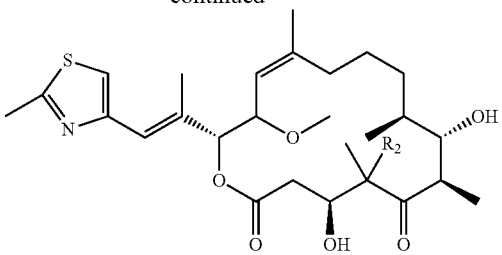

To a solution of 14-OH Epothilone D (which may be a 3,7-O-(tert-butyldimethylsilyl)-protected derivative) (1 equiv.) in 2 ml of dichloromethane is added trimethyloxonium tetrafluoroborate (3 equiv.) and N,N,N',N'-tetramethyl-naphthalene-1,8-diamine (3.5 equiv.). The reaction is stirred at 40° C. for 2 hours. The solution is diluted with 6 ml ethyl acetate, and washed with 2×10 ml water. The combined aqueous phase is extracted with ethyl acetate (2×15 ml), and dried over Na$_2$SO$_4$, filter and evaporated. The 14-O-methyl Epothilone D product is purified by SiO$_2$ chromatography. If a 3,7-O-(tert-butyldimethylsilyl) protected product exists, it shall be deprotected before purification by SiO$_2$ chromatography.

MS (ESI+) of 14-O-methyl Epothilone D Compound II-M (C$_{28}$H$_{43}$NO$_6$S): 522.3 [M+H]$^+$

EXAMPLE 5

Test of Biological Activity

Sulforhodamine B (SRB) test was used for screening the selective compounds of the present invention according to their anti-tumor activity on four different tumor cell lines. In SRB analysis, the cultured cells were trypsinized, counted and diluted to a suitable concentration (5000-7500 cells/100 µl) with a culture medium. The cells were inoculated into a 96-well microtiter plate at 100 µl suspension/well. After 20 hours, the test compounds which were diluted in the culture medium to 2×1000 nM~2×0.001 nM were added to each well. The cells were then cultured for 3 days, fixed with 100 µl 10% trichloroacetic acid at 4° C. for 1 hour, and then stained with 0.2% SRB/1% acetic acid at room temperature for 20 min. The unbound dye was rinsed with 1% acetic acid. The bound dye was dissolved with 200 µl 10 mM Tris-base. The amount of the bound dye was calculated from OD value detected at the wavelength of 515 nm. The amount of the bound dye was in direct proportion to the total amount of cell proteins. The data was analyzed with Kaleida Graph program, and the half inhibitory concentration (IC50) was calculated. Epothilones D and B were detected in parallel for Comparison. The results of the cytotoxicity experiments on the selected test compounds of the present invention are shown as follows. The other compounds of the present invention may also be detected with a similar method.

The action mechanism was detected by a cell-based tubulin polymerization assay. In the assay, MCF-7 cells cultured in a 35 mm dish were treated with 1 µM of the compound of the present invention at 37° C. for 1 hour. The cells were washed twice with 2 mL PBS without Ca and Mg, and then treated with 300 µL lysis solution (20 mM Tris, pH 6.8, 1 mM MgCl$_2$, 2 mM EDTA, 1% Triton X-100, with proteinase inhibitors) for 5-10 min to lyse the cells. The lysate was transferred to a 1.5-mL Eppendorf tube, and centrifuged at 18000 g for 12 min under room temperature. The supernatant containing soluble or unpolymerized tubulin was separated from the granular precipitate containing insoluble or polymerized tubulin and transferred to a new tube. The granular precipitate was re-suspended with 300 lysis solution. Each sample was analyzed by SDS-PAGE and Western-blot with anti-β-tubulin antibody (Sigma). The amount of β-tubulin on the blot was analyzed with NIH Image program for detecting changes of tubulin polymerization in the cells.

The tubulin polymerization assay demonstrated that the epothilone derivatives of the present invention had the same action mechanism as epothilones, and exhibited similar dynamics and efficacy under the test conditions. The other compounds according to the present invention may also be tested with the same method.

| Compounds | Half Inhibitory Concentration for Bacterial Growth (IC50, nM) | | | |
|---|---|---|---|---|
| | MCF-7 (Breast Cancer) | NCI/ADR-RES (MDR Breast Cancer) | SF-268 (Glioma) | NCl-H460 (Lung Cancer) |
| Epo D | 13 | 42 | 18 | 17 |
| Epo B | 0.5 | 5 | 0.8 | 0.7 |
| II-A | 7 | 12 | 6 | 7 |
| II-B | 0.1 | 0.5 | 0.2 | 0.2 |
| II-N | 2 | 7 | 3 | 2 |
| II-L | 0.05 | 0.1 | 1 | 0.5 |

INDUSTRIAL APPLICABILITY

The present invention relates to a series of epothilone compounds of general formula (I), preparation and pharmaceutical applications thereof. The epothilone compounds of the present invention are prepared from Epothilone D or a derivative thereof by biotransformation and chemical synthesis or chemical modification. The epothilone compounds of the present invention may be used for treating proliferative disorders, and can effectively inhibit excessive proliferation of cells and terminate cell growth, and thus are promising to become lead compounds for new anti-cancer drugs. Therefore, the present invention has industrial applicability.

We claim:

1. An epothilone compound represented by the following general formula (I):

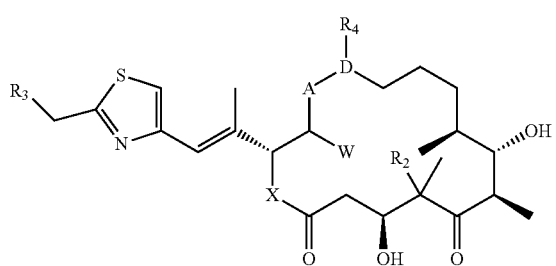

wherein,
A-D is carbon-carbon double bond of the following formula (a) or epoxy group of the following formula (b),

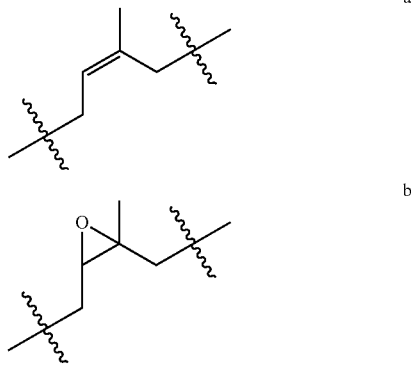

X is O;
W is $NR_1R$ or W is OR' provided that A-D is an epoxy group of formula (b), wherein R is selected from H, amino protective group, substituted or unsubstituted lower alkyl or unsaturated hydrocarbonyl; and R' is selected from substituted or unsubstituted lower alkyl or unsaturated hydrocarbonyl;

$R_1$ is selected from OH, substituted or unsubstituted lower alkyl or unsaturated hydrocarbonyl, or forms cycloalkyl together with R;

$R_2$ is selected from H, substituted or unsubstituted lower alkyl or unsaturated hydrocarbonyl, or forms lower cycloalkyl with the methyl on C-4 position;

$R_3$ is selected from H, OH or $NH_2$;

$R_4$ is methyl; or a pharmaceutically acceptable salt, hydrate, polymorph, optical isomer, racemate, diastereoisomer or enantiomer thereof.

2. The epothilone compound of claim 1, wherein W is $NR_1R$, wherein R is selected from amino protective group, substituted or unsubstituted $C_{1-6}$ alkyl or $C_{2-6}$ alkenyl; $R_1$ is selected from H, substituted or unsubstituted $C_{1-6}$ alkyl or $C_{2-6}$ alkenyl, or forms $C_{3-6}$ cycloalkyl together with R; or a pharmaceutically acceptable salt, hydrate, polymorph, optical isomer, racemate, diastereoisomer or enantiomer thereof.

3. The epothilone compound of claim 1, wherein W is NH—$CH_3$, N($CH_3$)$_2$ or

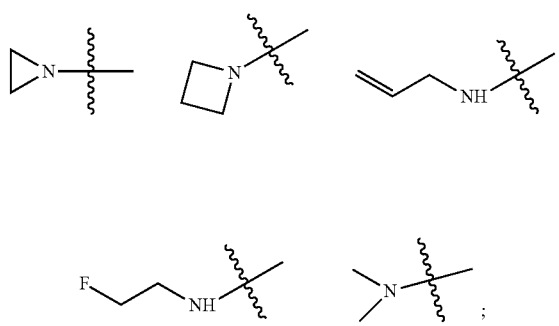

$R_2$ is H or methyl;
or a pharmaceutically acceptable salt, hydrate, polymorph, optical isomer, racemate, diastereoisomer or enantiomer thereof.

4. An epothilone compound selected from the following compounds:
II-A
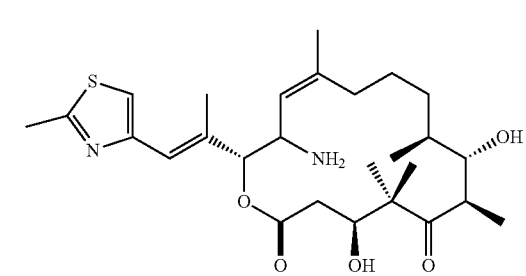
II-B
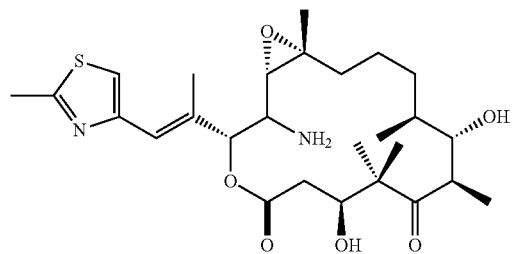
II-C
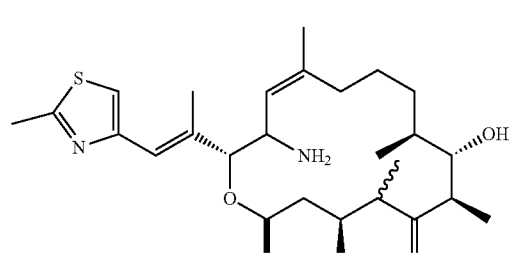
II-D
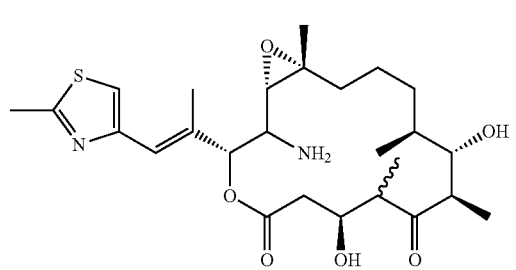
II-E
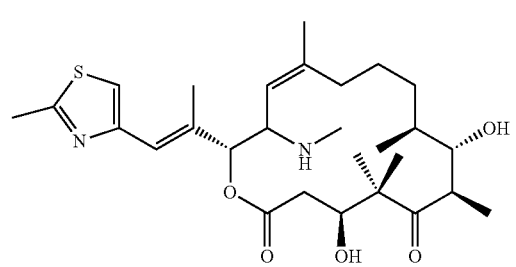
II-F
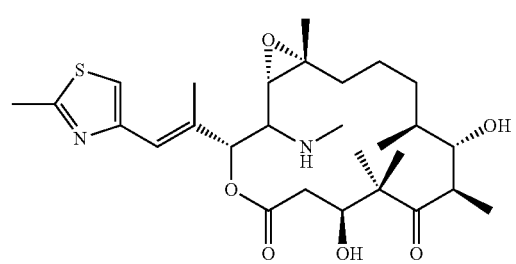
-continued
II-H
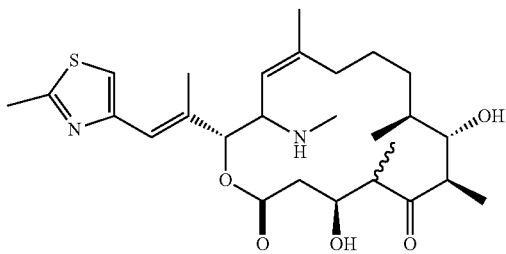
II-J
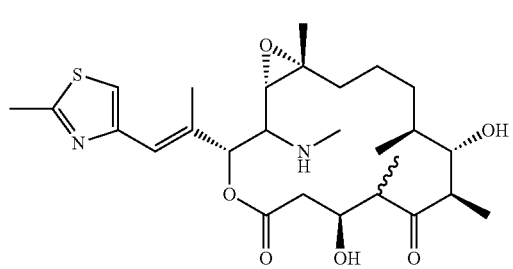
II-K
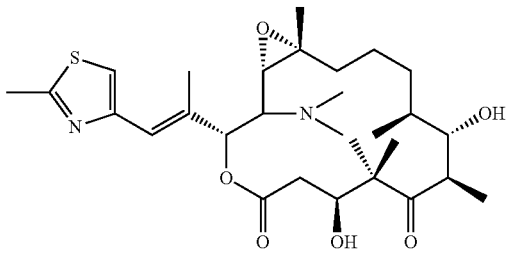
II-L
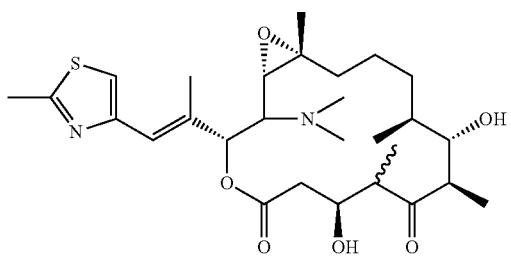
II-N
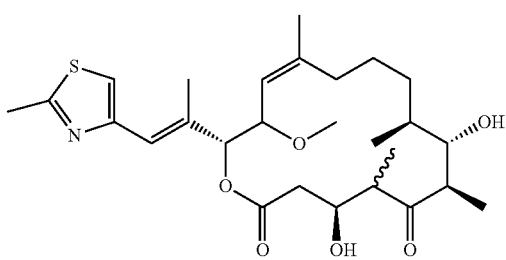
II-O
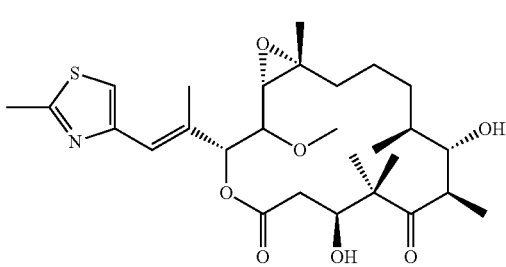

-continued

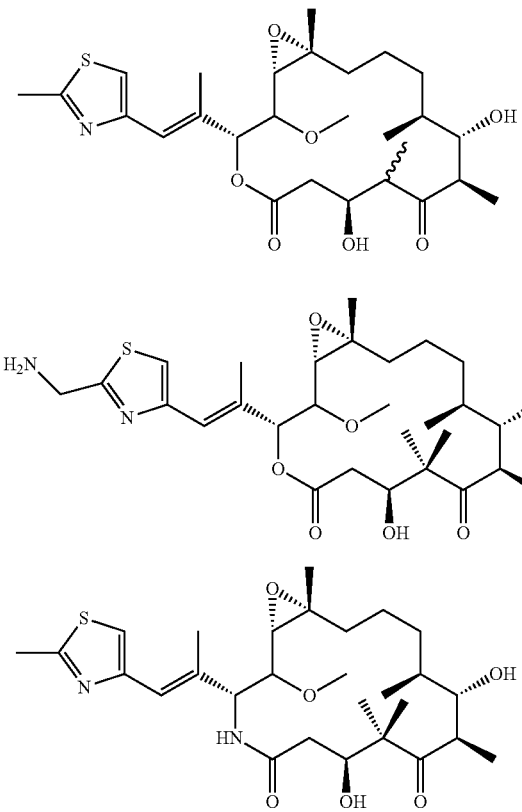

or a pharmaceutically acceptable salt, hydrate, polymorph, optical isomer, racemate, diastereoisomer or enantiomer thereof.

5. A pharmaceutical composition comprising the epothilone compound of claim 1 or a pharmaceutically acceptable salt, hydrate, polymorph, optical isomer, racemate, diastereoisomer or enantiomer thereof, and one or more pharmaceutical carriers and/or diluents.

6. The composition of claim 5, further comprising one or more other active agents.

7. The pharmaceutical composition of claim 5, wherein W is $NR_1R$, wherein R is selected from amino protective group, substituted or unsubstituted $C_{1-6}$ alkyl or $C_{2-6}$ alkenyl; $R_1$ is selected from H, substituted or unsubstituted $C_{1-6}$ alkyl or $C_{2-6}$ alkenyl, or forms $C_{3-6}$ cycloalkyl together with R.

8. The pharmaceutical composition of claim 5, wherein W is $NH-CH_3$, $N(CH_3)_2$ or

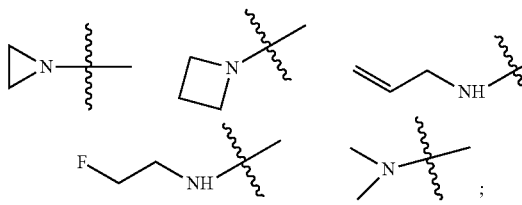

$R_2$ is H or methyl.

9. A pharmaceutical composition comprising an epothilone compound selected from the following compounds, or a pharmaceutically acceptable salt, hydrate, polymorph, optical isomer, racemate, diastereoisomer or enantiomer thereof, and one or more pharmaceutical carriers and/or diluent:

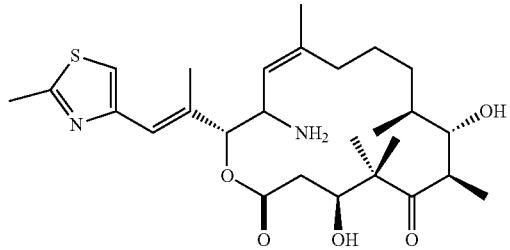
II-A

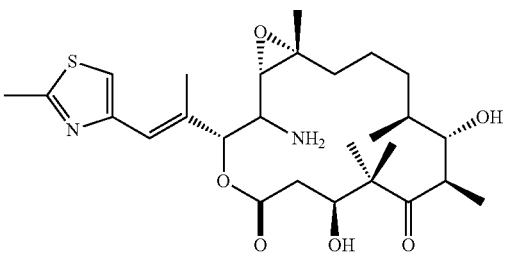
II-B

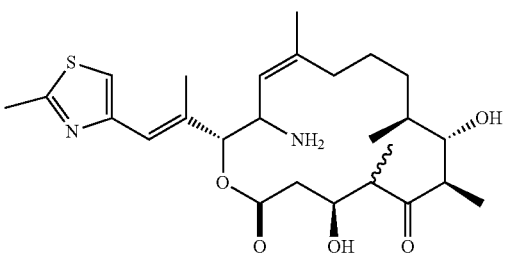
II-C

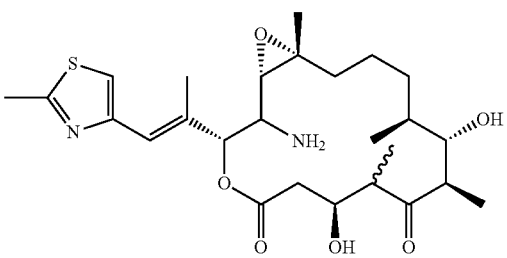
II-D

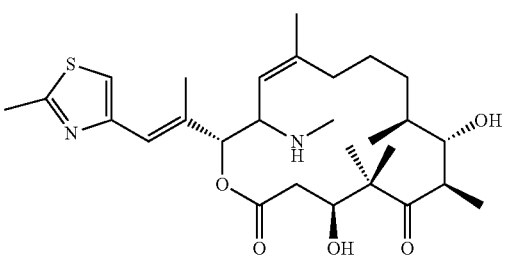
II-E

II-F
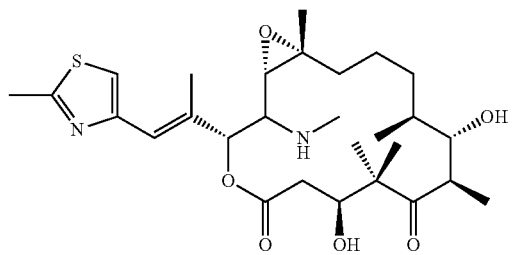

II-H
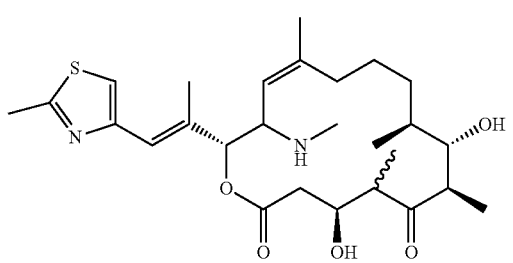

II-J
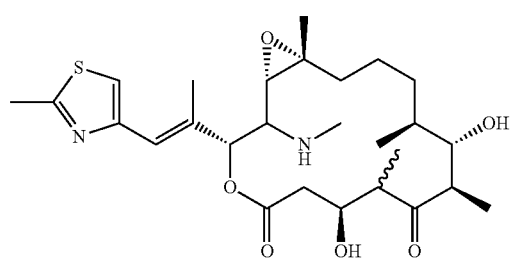

II-K
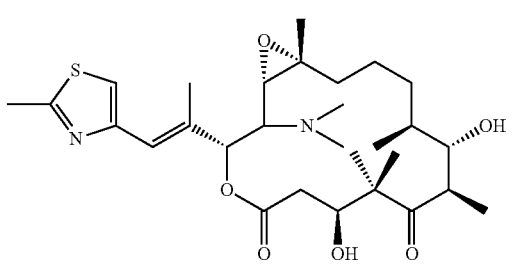

II-L
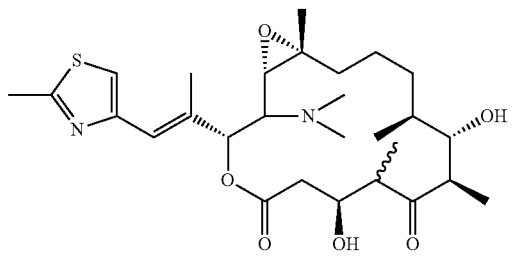

II-N
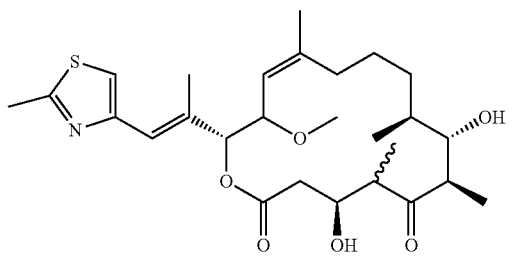

II-O
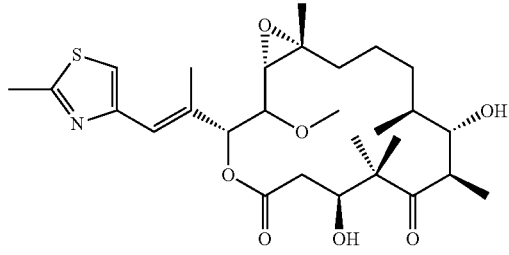

II-P
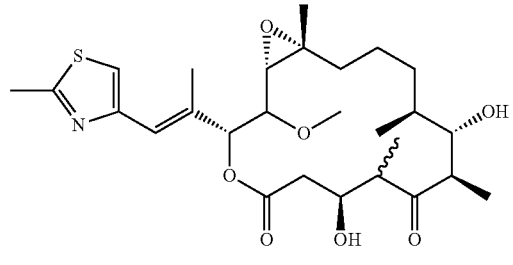

II-Q
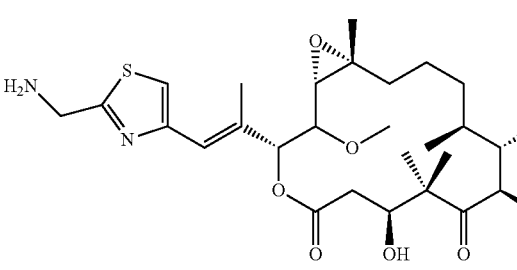

II-R
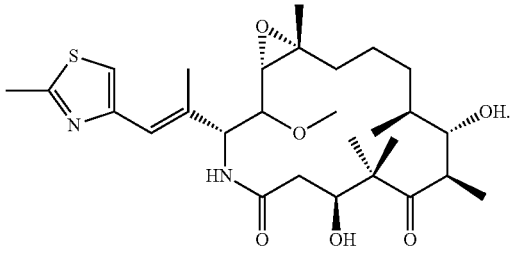

10. A method for treating proliferative disorders selected from the group consisting of tumors, multiple sclerosis, rheumatoid arthritis, atherosclerosis and restenosis, comprising administering a therapeutically effective amount of an epothilone compound of claim 1 or a pharmaceutically acceptable salt, hydrate, polymorph, optical isomer, racemate, diastereoisomer or enantiomer thereof to a subject in need thereof.

11. The method of claim 10, wherein W is $NR_1R$, wherein R is selected from amino protective group, substituted or unsubstituted $C_{1-6}$ alkyl or $C_{2-6}$ alkenyl; $R_1$ is selected from H, substituted or unsubstituted $C_{1-6}$ alkyl or $C_{2-6}$ alkenyl, or forms $C_{3-6}$ cycloalkyl together with R.

12. The method of claim 10, wherein W is NH—$CH_3$, $N(CH_3)_2$ or

-continued
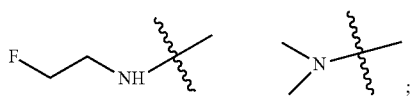
R$_2$ is H or methyl; and
R$_4$ is CH$_3$.
13. The method of claim 10, wherein the epothilone compound is selected from the following compounds:
II-A
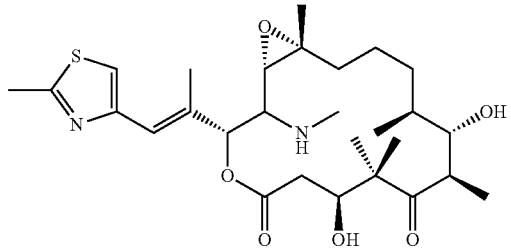
II-B
II-C
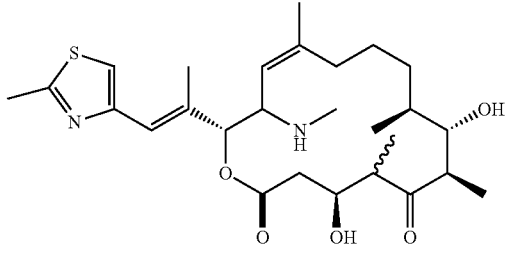
II-D
II-E
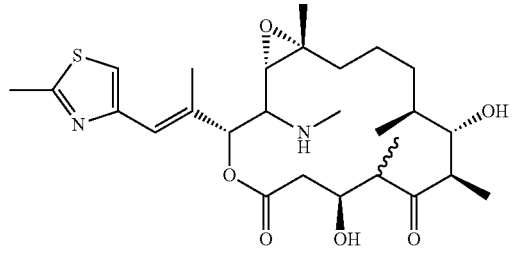
-continued
II-F
II-H
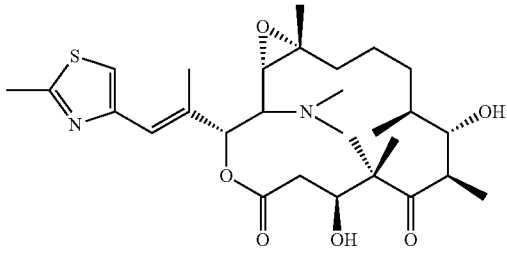
II-J
II-K
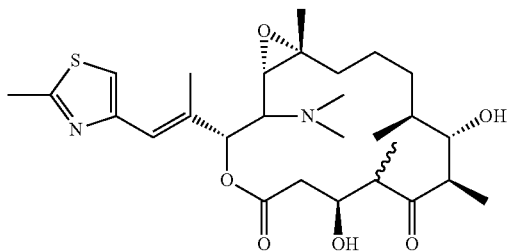
II-L
II-N
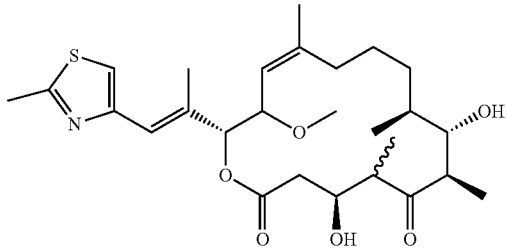

II-O
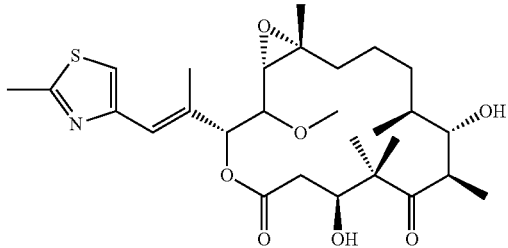
II-P
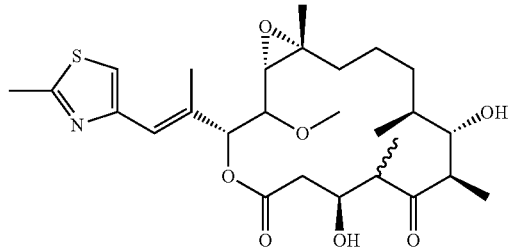
II-Q
II-R
14. A method for inhibiting excessive proliferation of cells and terminating cell growth, comprising contacting the cell with an epothilone compound of claim 1 or a pharmaceutically acceptable salt, hydrate, polymorph, optical isomer, racemate, diastereoisomer or enantiomer thereof.
* * * * *

UNITED STATES PATENT AND TRADEMARK OFFICE
CERTIFICATE OF CORRECTION

PATENT NO. : 8,895,590 B2  
APPLICATION NO. : 13/526097  
DATED : November 25, 2014  
INVENTOR(S) : Tang et al.

Page 1 of 1

It is certified that error appears in the above-identified patent and that said Letters Patent is hereby corrected as shown below:

Title page item (30), the foreign priority application should read as follows:

-- (30) Foreign Application Priority Data
Dec. 17, 2009 (CN) 2009 10259234.7 --

Signed and Sealed this
Third Day of March, 2015

Michelle K. Lee
*Deputy Director of the United States Patent and Trademark Office*